(12) United States Patent
Luo

(10) Patent No.: US 11,975,149 B1
(45) Date of Patent: May 7, 2024

(54) LOW-NOISE BREATHING MASK

(71) Applicant: DCSTAR INC, New York, NY (US)

(72) Inventor: David Luo, New York, NY (US)

(73) Assignee: DCSTAR INC, New York, NY (US)

( * ) Notice: Subject to any disclaimer, the term of this patent is extended or adjusted under 35 U.S.C. 154(b) by 0 days.

(21) Appl. No.: 18/324,261

(22) Filed: May 26, 2023

(51) Int. Cl.
*A61M 16/06* (2006.01)

(52) U.S. Cl.
CPC ......... *A61M 16/06* (2013.01); *A61M 2205/42* (2013.01)

(58) Field of Classification Search
CPC ... A61B 5/0205; A61B 5/02405; A61B 5/087; A61B 5/0876; A61B 5/091; A61B 5/363; A61B 5/4809; A61B 5/4812; A61B 5/4818; A61B 5/4836; A61D 7/00; A61F 2007/0003; A61F 2007/0061; A61F 7/10; A61M 16/00; A61M 16/0003; A61M 16/0045; A61M 16/0051; A61M 16/0057; A61M 16/0063; A61M 16/0066; A61M 16/0069; A61M 16/009; A61M 16/024; A61M 16/026; A61M 16/0488; A61M 16/06; A61M 16/0605; A61M 16/0611; A61M 16/0616; A61M 16/0622; A61M 16/0633; A61M 16/0638; A61M 16/0644; A61M 16/065; A61M 16/0655; A61M 16/0666; A61M 16/0672; A61M 16/0683; A61M 16/0694; A61M 16/08; A61M 16/0808; A61M 16/0816; A61M 16/0825; A61M 16/0833; A61M 16/085; A61M 16/0858; A61M 16/0866; A61M 16/0875; A61M 16/10; A61M 16/1045; A61M 16/1055; A61M 16/1065; A61M 16/107; A61M 16/109; A61M 16/1095; A61M 16/16; A61M 16/20; A61M 16/201; A61M 16/202; A61M 16/205; A61M 16/206; A61M 16/208; A61M 16/209; A61M 16/22; A61M 2016/0027; A61M 2016/003;

(Continued)

(56) References Cited

U.S. PATENT DOCUMENTS 5,240,479 A * 8/1993 Bachinski ............ B01D 46/521
  55/528
6,581,594 B1 * 6/2003 Drew ................ A61M 16/0644
  128/207.12

(Continued)

*Primary Examiner* — Annette Dixon
(74) *Attorney, Agent, or Firm* — HSML P.C.

(57) ABSTRACT

A low-noise breathing mask includes an elastic liner, a mask body, and a noise reduction component. The noise reduction component includes a ventilation opening and a muffler. The ventilation opening is provided on the mask body and communicates with a third opening. The muffler is connected to the mask body and covers the ventilation opening. The muffler has a first surface facing the external environment and a second surface opposite to the first surface. The first surface has a first breathable area exposed to the external environment, and the second surface has a second breathable area exposed to the cavity. The muffler also has multiple breathable channels that communicate with the first and the second breathable area, allowing gas in the cavity to be discharged to the external environment through the muffler. The multiple breathable channels in the muffler can render the gas flow smaller and less turbulent.

18 Claims, 18 Drawing Sheets

(58) Field of Classification Search
CPC .. A61M 2016/0033; A61M 2016/0036; A61M 2016/0042; A61M 2016/0661; A61M 2202/0085; A61M 2202/0208; A61M 2202/0225; A61M 2205/02; A61M 2205/0205; A61M 2205/0216; A61M 2205/0238; A61M 2205/14; A61M 2205/15; A61M 2205/21; A61M 2205/3303; A61M 2205/332; A61M 2205/3331; A61M 2205/3334; A61M 2205/3344; A61M 2205/3368; A61M 2205/3379; A61M 2205/3569; A61M 2205/3592; A61M 2205/3606; A61M 2205/362; A61M 2205/3653; A61M 2205/42; A61M 2205/50; A61M 2205/581; A61M 2205/583; A61M 2205/75; A61M 2205/7527; A61M 2205/7536; A61M 2206/14; A61M 2207/00; A61M 2210/0618; A61M 2210/0625; A61M 2230/005; A61M 2230/04; A61M 2230/202; A61M 2230/40; A61M 2230/60; A61M 2230/63; A61M 2250/00; A61M 39/10; A61M 39/1055; A62B 18/006; A62B 18/02; A62B 18/025; A62B 18/08; A62B 18/082; A62B 18/10; A62B 19/00; A62B 23/025; A62B 7/10; A62B 9/02; A62B 9/04; B23P 11/02; F16K 11/072; F16K 11/0873; F16K 5/0407; F24C 7/065; G01F 1/28; Y10S 128/912; Y10S 137/908; Y10T 137/2617; Y10T 137/7781; Y10T 137/7786; Y10T 29/49; Y10T 29/49872

See application file for complete search history.

(56) References Cited

U.S. PATENT DOCUMENTS

| | | | | |
|---|---|---|---|---|
| 2003/0079751 | A1* | 5/2003 | Kwok | B23P 11/02 128/206.15 |
| 2010/0051034 | A1* | 3/2010 | Howard | A61M 16/0816 128/207.11 |
| 2015/0151065 | A1* | 6/2015 | Frater | A61M 16/0611 128/205.25 |
| 2015/0352306 | A1* | 12/2015 | Scheiner | A61M 16/10 128/205.25 |

* cited by examiner

LOW-NOISE BREATHING MASK

TECHNICAL FIELD

The present disclosure relates to the field of medical equipment technology, specifically to medical devices related to obstructive sleep apnea, and more specifically, to a low-noise breathing mask.

BACKGROUND

Obstructive sleep apnea is a common sleep breathing disorder characterized by breathing pauses and low airflow due to narrowed pharyngeal airway during sleep. This condition can cause patients to experience breathing pauses during sleep, with at least 30 episodes of breathing pauses occurring in 7 hours of sleep for adults, with each episode lasting for at least 10 seconds during which nasal airflow stops. Oxygen saturation drops by 4% or more during breathing pauses, or the apnea-hypopnea index is greater than 5 times per hour. Obstructive sleep apnea can cause chronic intermittent hypoxia and fragmented sleep, accompanied by physiological changes such as hypoxemia and hypercapnia, and can easily cause multi-system damage or complications such as coronary heart disease, hypertension, and diabetes.

Obstructive sleep apnea is usually treated with continuous positive airway pressure therapy, which involves using a CPAP machine to provide positive pressure ventilation, delivering gas to the patient's airway to guide normal breathing.

In some cases, the treatment system used for treatment may include a noise-reducing exhaust device to allow for the exhalation of carbon dioxide. The noise-reducing exhaust device can allow exhaled gas to flow from the inside of the mask to the outside of the mask, such as into the environment. Once the treatment system is in operation, a relatively sealed environment is formed, with the patient's inhalation and exhalation occurring in this small space. If this system does not have a noise-reducing exhaust device, or the noise-reducing exhaust device is not designed properly, it is easy to inhale carbon dioxide again, or even cause or exacerbate carbon dioxide retention in this environment, which is very detrimental to health. In case of a sudden power failure or other emergency situation, the patient can use the noise-reducing exhaust device to breathe and exchange air to prevent suffocation. Therefore, the noise-reducing exhaust device is a very important structure in the entire continuous positive airway pressure therapy system.

For patients or their partners who share beds, the noise generated by exhaust is an important issue during the treatment process. Excessive noise can make it difficult for patients or partners to fall asleep. The common noise reduction can use an exhaust device on the mask that can be directly opened holes on the mask, and the exhaled gas is discharged directly from the hole. This airflow is relatively concentrated, however, and can still generate noise. Moreover, if the hole design is improper, the gas flowing through the hole may produce a whistling sound, which can affect the quality of sleep.

SUMMARY

The technical problem solved by this disclosure is to provide a low-noise breathing mask that can disperse airflow, reduce the noise during airflow discharge, improve the user's sleep quality, provide a better user experience, and help improve user-friendliness in the treatment process, while avoiding resource waste caused by frequent replacement.

To solve the above technical problem, the technical solution adopted by the disclosure is to provide a low-noise breathing mask, including: an elastic liner having a fitting side for contacting the user's face and a first connecting side opposite to the fitting side; the fitting side is provided with a first opening through which the user's mouth and nose can pass, and the first connecting side is provided with a second opening that communicates with the first opening; a mask body having a second connecting side and a third connecting side opposite to each other, the second connecting side is provided with a third opening that matches the second opening, the third opening is connected to the second opening, and the third connecting side is provided with a fourth opening for receiving pressurized gas; the mask body also has a cavity communicating between the third opening and the fourth opening; and a noise reduction component, including a ventilation opening and a muffler, the ventilation opening is provided on the mask body and communicates with the third opening, the muffler is connected to the mask body and covers the ventilation opening, the muffler has a first surface facing the external environment and a second surface opposite to the first surface, the first surface has a first breathable area exposed to the external environment, and the second surface has a second breathable area exposed to the cavity; the muffler also has multiple breathable channels that communicate the first breathable area and the second breathable area, allowing gas in the cavity to be discharged to the external environment.

By adopting the above technical solution of the low-noise breathing mask, the mask has at least one noise reduction component that replaces the directly opened holes on the mask in the existing technology. The noise reduction component is set on the wall surface of the mask body that is not in direct contact with the face of the user. One of the key points is that the noise reduction component includes a ventilation opening and a muffler. The ventilation opening penetrates the mask body to connect the cavity with the external environment, and the muffler is connected to the mask body and covers the ventilation opening. The muffler can be made of noise reduction materials. Specifically, the muffler has a first surface and a second surface, the first surface corresponds to the side facing the external environment, and the second surface corresponds to the side facing the cavity (referred to as the pressurization chamber in this field) and the face. At the same time, the muffler has multiple breathable channels that communicate the first breathable area and the second breathable area. It can be understood that after the gas produced by exhalation enters the cavity, it forms another exhaust flow path different from the pressurized airflow in the cavity. The exhaled gas is smoothly guided to the noise reduction component and discharged to the external environment through the breathable channels of the muffler. That is to say, the muffler allows the gas inside the cavity to be discharged to the external environment through the muffler. Therefore, when wearing the low-noise breathing mask, the gas exhaled by the user, such as carbon dioxide, can continue to be discharged from the inside of the cavity (referred to as the pressurization chamber in this field) through the noise reduction component to the external environment. Among them, multiple breathable channels contained in the muffler can play a role in dispersing the airflow, so that the bundled airflow is dispersed into smaller airflows, thereby significantly reducing the noise, e.g., softer, when the gas in the cavity is discharged to the external environment through the muffler, and the noise reduction effect is surprisingly higher. In addition, since the gas exhaled by the user can continuously flow from the inside of the cavity to the external environment, setting the noise reduction component can reduce the probability of the exhaled carbon dioxide being inhaled again, and at the same time, maintain the therapeutic pressure in the cavity during use.

The present disclosure provides a low-noise breathing mask. In the mask, the surface area of the first breathable area is between 0.45% to 45% of the outer surface area of the mask body, where the outer surface of the mask body is exposed to the external environment. The muffler provides enough area for gas inside the cavity to be discharged smoothly to the external environment through the muffler, without compromising the overall structural strength of the mask.

In the low-noise breathing mask, the mask body also includes a shielding wall with a thickness of less than or equal to 5 mm, with the ventilation opening set in the shielding wall. The muffler has a thickness of less than or equal to 15 mm and a weight of less than or equal to 7 g. The area of the first or second breathable area is at or between 1-2000 $mm^2$. The muffler can be made of noise-reducing cotton or mesh, where the noise-reducing cotton is made of polyester, polypropylene, polyethylene, nylon, vinyl or natural fabric, and the noise reducing mesh is made of one of polyvinyl chloride, polypropylene, polytetrafluoroethylene or nylon. The material, thickness, density, etc. of the muffler determine its noise reduction effect, but the specific requirements need to be jointly determined based on processing, aesthetics, and actual performance. However, the thickness of the muffler should not be too thick, as it will reduce the gas permeability, affect the appearance and weight of the mask body. Therefore, the thickness and weight of the noise reducing material (that is, the muffler) should not exceed 15 mm and 7 g respectively. And the area of the first breathable area or the second breathable area is at or between 1-2000 $mm^2$. The thickness of the noise reduction material refers to the vertical distance from the first surface to the second surface of the noise reduction material. With this design, when the exhaled gas is guided to the noise reduction component, the noise generated when the exhaled gas passes through the noise reduction component and enters the external environment does not exceed 30 dB.

In the above low-noise breathing mask provided by the present disclosure, the low-noise breathing mask includes multiple noise reduction components, which can increase the exhaust channels and ensure smooth discharge of gas in the cavity.

In the above low-noise breathing mask provided by the present disclosure, the contour of the ventilation opening can be circular, elliptical, rectangular, square, or triangular. It should be understood that the ventilation opening can also have other suitable shapes to guide the exhaust gas.

In the above low-noise breathing mask provided by the present disclosure, the noise reduction component also includes a casing, and the muffler is attached to one side surface of the casing facing the cavity. The casing has at least one through exhaust port and can be detachably connected to the mask body. Specifically, the casing and the mask body are connected by an adhesive, snap fastener (setting a snap-fastener structure on the casing and the mask body for connection), buckle, Velcro, knob, magnetic component (installing magnets on the casing and the mask body for connection), or clip (setting a clip on the casing and the mask body for connection).

In this way, when the air permeability of the muffler is reduced, it can be quickly replaced or removed for washing without having to treat the entire low-noise breathing mask.

In the above low-noise breathing mask provided by the present disclosure, the muffler is fixedly connected to the mask body. Specifically, the muffler and the mask body are connected by an adhesive, snap fastener (setting a snap-fastener structure on the muffler and the mask body for connection), buckle, knob, injection molding, ultrasonic welding (using an ultrasonic machine to connect the muffler and the mask body together), or heat pressing. In this way, the connection between the muffler and the mask body is more stable and less likely to disconnect or fall off.

In the above-mentioned low-noise breathing mask provided by the present disclosure, the angle between the plane where the first breathable area of the first surface of the muffler is located and the plane where the part of the inner surface of the mask body connected to the muffler is located is 0-80°. This reduces the possibility of airflow spraying onto the wearer's face during exhaust and affecting their sleep.

In the above low-noise breathing mask provided by the present disclosure, the minimum distance between the second surface of the muffler and the plane where the first opening is located is greater than or equal to the preset value (10 mm), so that when the low-noise breathing mask is worn on the face, the minimum distance between the muffler and the face is greater than or equal to 10 mm. It should be understood that the direction of exhaust should be avoided from blowing towards the face or other parts that may affect the wearer's sleep, while also avoiding the blockage of the noise reduction component during side sleep. Therefore, the noise reduction component should be positioned at a certain distance from the face, and the distance between the noise reduction component and the face in the use state should be at least 10 mm to avoid discomfort caused by compression of the noise reduction component on the face.

To solve the above-mentioned technical problems, the disclosure provides another low-noise breathing mask. The low-noise breathing mask includes: an elastic liner having a fitting side for contacting the user's face and a first connecting side opposite to the fitting side; the fitting side has a first opening for the mouth and nose to pass through, and the first connecting side has a second opening in communication with the first opening; a mask body having a second connecting side and a third connecting side opposite to each other, the second connecting side having a third opening matching the second opening, the third opening being connected to the second opening, and the third connecting side having a fourth opening for receiving pressurized gas; the mask body also has a cavity communicating between the third opening and the fourth opening; a noise reduction component including a ventilation opening and a muffler, the ventilation opening being provided on the elastic liner, and the muffler having a first surface facing the external environment and a second surface opposite to the first surface, the first surface having a first breathable area exposed to the external environment, and the second surface having a second breathable area exposed to the cavity; the muffler also has multiple breathable channels communicating the first breathable area and the second breathable area, thereby allowing the gas in the cavity to be continuously discharged to the external environment through the muffler.

Obviously, when wearing the aforementioned low-noise breathing mask, the gas exhaled by the user, such as carbon dioxide, can continuously be discharged to the external environment through the noise reduction component from the interior of the aforementioned cavity (referred to as the pressurization chamber in this field). The multiple breathable channels contained in the muffler component can play a role in dispersing the airflow, making the bulk flow into smaller, less turbulent streams, thereby significantly reducing the noise when the gas inside the cavity is discharged to the external environment through the muffler, resulting in significant noise reduction.

In the above-mentioned low-noise breathing mask provided by the disclosure, multiple noise reduction components are arranged symmetrically or asymmetrically on the elastic liner, which can increase the exhaust channel and ensure smooth discharge of gas in the cavity.

To solve the above-mentioned technical problems, the disclosure provides another low-noise breathing mask, which includes an elastic liner having a fitting side for contacting the user's face and a first connecting side opposite to the fitting side; the fitting side has a first opening for the mouth and nose to pass through, and the first connecting side has a second opening in communication with the first opening; a mask body having a second connecting side and a third connecting side opposite to each other, the second connecting side having a third opening matching the second opening, the third opening being connected to the second opening, and the third connecting side having a fourth opening for receiving pressurized gas; the mask body also has a cavity communicating between the third opening and the fourth opening; a noise reduction component including a ventilation opening and a muffler, the ventilation opening provided on the mask body and communicating with the third opening, the muffler being connected to the mask body and covering the ventilation opening, the muffler having a first surface facing the external environment and a second surface opposite to the first surface, the first surface having a first breathable area exposed to the external environment, and the second surface having a second breathable area exposed to the cavity; the muffler also has multiple breathable channels communicating the first breathable area and the second breathable area, thereby allowing the gas in the cavity to be continuously discharged to the external environment through the muffler. The surface area of the first breathable area is at or between 0.45% to 45% of the surface area of the outer surface of the mask body, where the outer surface of the mask body is in communication with the external environment. The mask body has a shielding wall with a thickness of less than or equal to 5 mm, and the ventilation opening is provided in the shielding wall.

To solve the above technical problems, the disclosure provides another type of low-noise breathing mask, which includes: an elastic liner with a fitting side for contacting the user's facial area and a first connecting side opposite the fitting side. The fitting side is provided with a first opening for the mouth and nose to pass through, while the first connecting side has a second opening that communicates with the first opening. The mask body has a second connecting side and a third connecting side that are opposite each other. The second connecting side has a third opening that matches the second opening, and the third opening is connected to the second opening. The third connecting side has a fourth opening for receiving pressurized gas. The mask body also has a cavity communicating between the third opening and the fourth opening. A noise reduction component includes a ventilation opening and a muffler. The ventilation opening is provided on the mask body and communicates with the third opening, while the muffler is connected to the mask body and covers the ventilation opening. The muffler has a first surface facing the external environment and a second surface opposite the first surface. The first surface has a first breathable area exposed to the external environment, and the second surface has a second breathable area exposed to the cavity. The muffler also has multiple breathable channels that communicate with the first breathable area and the second breathable area, allowing gas inside the cavity to be discharged to the external environment through the muffler. The muffler has a thickness less than or equal to 15 mm, and the area of the first breathable area or the second breathable area is at or between 1-2000 mm$^2$. The weight of the muffler is less than or equal to 7 g.

The low-noise breathing mask implemented by the disclosure can achieve the following beneficial effects of at least: The low-noise breathing mask sets at least one noise reduction component to replace the prior use of directly opened holes on the mask. Instead, the noise reduction component is set on the wall of the breathing mask that is not in direct contact with the user's facial area. One of the most critical aspects is that the noise reduction component includes a ventilation opening and a muffler. The ventilation opening penetrates the breathing mask to communicate the cavity with the external environment. The muffler is connected to the mask body and covers the ventilation opening, which can be made of noise reduction materials. Specifically, the muffler has a first surface and a second surface. The first surface corresponds to the side facing the external environment, and the second surface corresponds to the side facing the cavity (referred to as the pressurization chamber in this field) and the face. Moreover, the muffler has multiple breathable channels that communicate with the first breathable area and the second breathable area. It can be understood that after the gas exhaled by the user enters the cavity, another exhaust flow path different from the pressurized airflow is formed in the cavity. The exhaled gas is smoothly guided to the noise reduction component and discharged to the external environment through the breathable channels of the muffler. Therefore, when wearing the low-noise breathing mask, the gas exhaled by the user, such as carbon dioxide, can continuously be discharged to the external environment from the interior of the cavity (referred to as the pressurization chamber in this field) through the noise reduction component. The multiple breathable channels contained in the muffler can disperse the airflow, making the bundled airflow disperse into more gentle small streams. This greatly reduces the sound when the gas inside the cavity is discharged to the external environment through the muffler, and the noise reduction effect is significant.

In addition, since the gas exhaled by the user can continuously flow from the inside of the cavity to the external environment, setting the noise reduction component can reduce the probability of the user inhaling carbon dioxide again, and also maintain the size of the therapeutic pressure in the cavity during use.

BRIEF DESCRIPTION OF THE DRAWINGS

To illustrate the technical solutions in the embodiments or prior art more clearly, the following will briefly introduce the drawings needed in the description of the embodiments or prior art. Obviously, the following description of the drawings is only for the embodiments of the disclosure. Ordinary skilled persons in the field can obtain other drawings based on the provided drawings without creative labor.

DESCRIPTION OF REFERENCE NUMERALS IN SPECIFIC IMPLEMENTATIONS

| Low-noise breathing mask | 1 |
| --- | --- |
| Elastic liner | 3 |
| Muffler | 41 |
| External environment | 43 |
| First surface | 411 |
| Thickness of muffler | T |
| Casing | 45 |
| Liner side surface | 32 |
| Second opening | 302 |
| Fourth opening | 202 |
| Mask body | 2 |
| Noise reduction component | 4 |
| Ventilation opening | 42 |
| Cavity | 44 |
| Second surface | 412 |
| Thickness of the ventilation opening | H |
| Liner extension surface | 31 |
| First opening | 301 |
| Third opening | 201 |
| Shielding wall | 203 |

DETAILED DESCRIPTION

In order to facilitate the understanding of the disclosure, the following will provide a more comprehensive description of the disclosure with reference to the accompanying drawings. The drawings show typical embodiments of the disclosure. However, the disclosure can be implemented in many different forms, and is not limited to the embodiments described in this article. On the contrary, the purpose of providing these embodiments is to make the disclosure of the disclosure more thorough and comprehensive.

Unless otherwise defined, all technical and scientific terms used in this article have the same meaning as those generally understood by those skilled in the art to which the disclosure pertains. The terms used in the specification of the disclosure are only intended to describe specific embodiments and are not intended to limit the disclosure.

Embodiment 1

Figure 1:
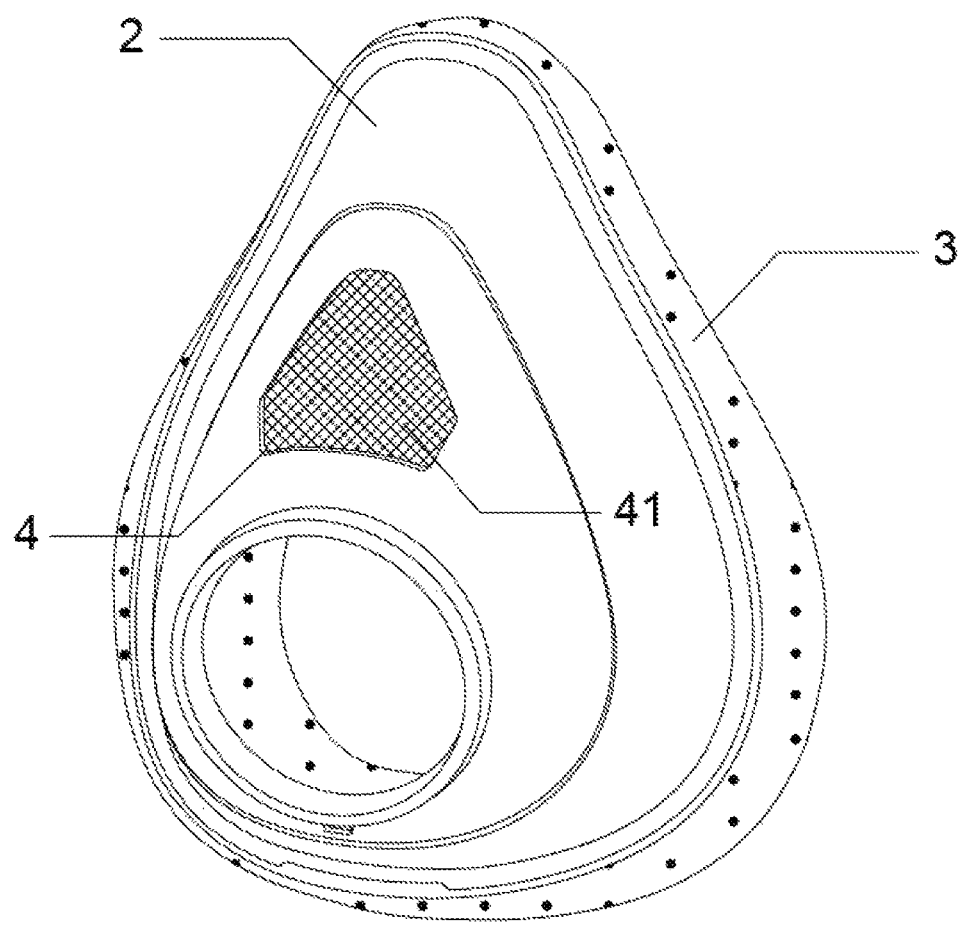
FIG. 1 is a three-dimensional combined schematic diagram of a low-noise breathing mask provided in Embodiment 1.
Figure 2:
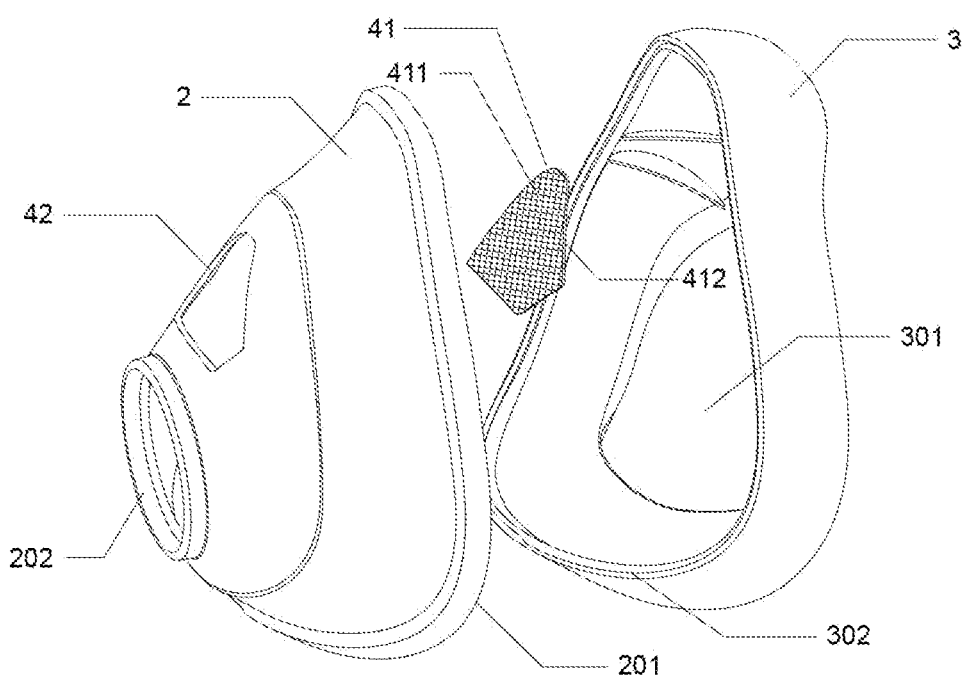
FIG. 2 is a three-dimensional exploded schematic diagram of the low-noise breathing mask provided in Embodiment 1.
Figure 3:
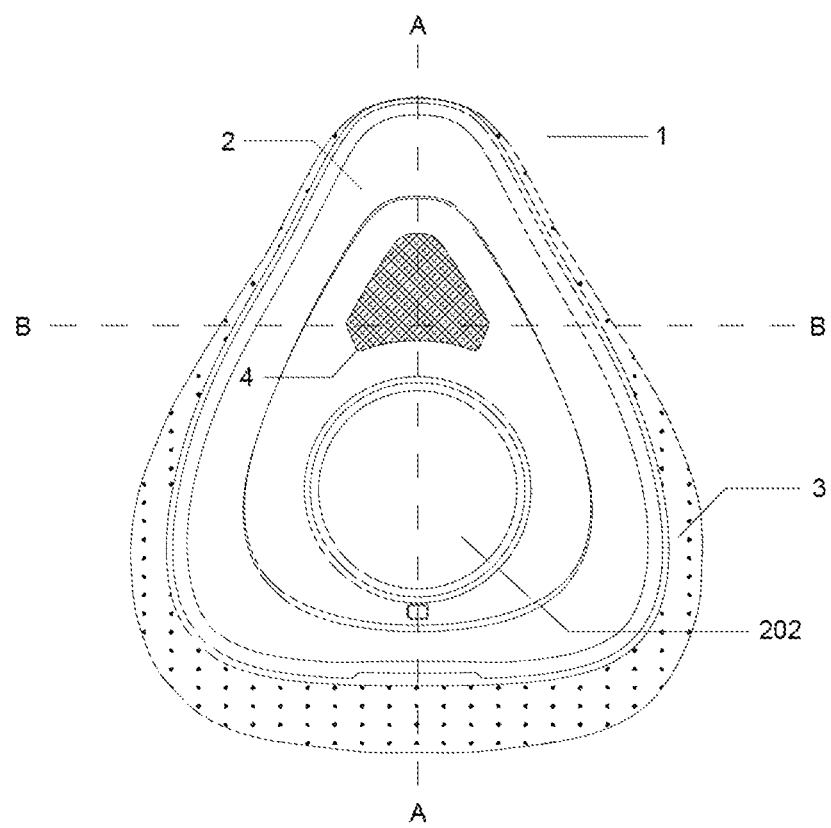
FIG. 3 is a schematic diagram of the front view of the low-noise breathing mask provided in Embodiment 1.

The present embodiment provides a low-noise breathing mask 1, as shown in FIGS. 1-3. FIG. 1 is a three-dimensional combined schematic diagram of the low-noise breathing mask 1 provided in this embodiment, FIG. 2 is an exploded perspective diagram of the low-noise breathing mask 1 provided in this embodiment, and FIG. 3 is a front view diagram of the low-noise breathing mask 1 provided in this embodiment. As shown in FIGS. 1-3, the low-noise breathing mask 1 includes an elastic liner 3, a mask body 2, and a noise reduction component 4.

Figure 4:
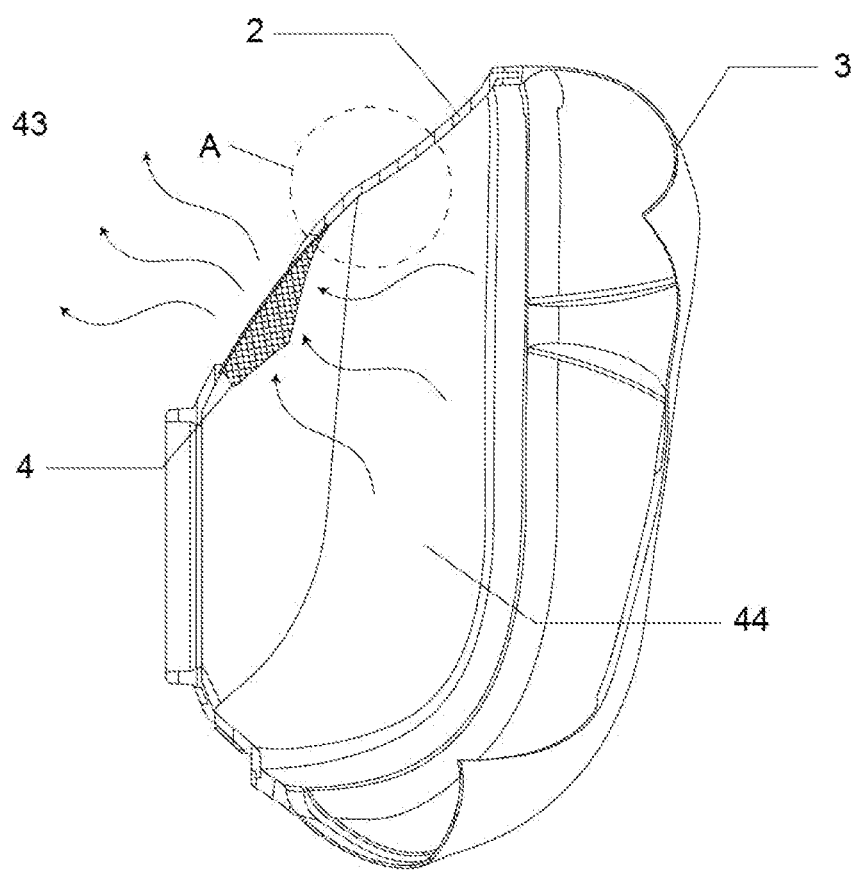
FIG. 4 is a schematic diagram of the sectional view taken at A-A of FIG. 3.

The elastic liner 3 has a fitting side for contacting the user's face and a first connecting side opposite to the fitting side. The fitting side is provided with a first opening 301 through which the user's mouth and nose can pass. The first connecting side is provided with a second opening 302 that communicates with the first opening 301. The mask body 2 has a second connecting side and a third connecting side that are opposite to each other. The second connecting side is provided with a third opening 201 that matches the second opening 302. The third opening 201 is connected to the second opening 302, and the third connecting side is provided with a fourth opening 202 for receiving pressurized gas. Refer to FIG. 4, which is a sectional view taken along line A-A of FIG. 3, and the internal structure of the low-noise breathing mask 1 can be seen in FIG. 4. As shown in FIG. 4, the mask body 2 also has a cavity 44 that communicates between the third opening 201 and the fourth opening 202. The noise reduction component 4 includes a ventilation opening 42 and a muffler 41. The ventilation opening 42 is provided on the mask body 2 and communicates with the third opening 201. The contour of the ventilation opening 42 is hexagonal. The muffler 41 is connected to the mask body 2 and covers the ventilation opening 42. The muffler 41 has a first surface 411 facing the external environment 43 and a second surface 412 opposite to the first surface 411. The first surface 411 has a first breathable area exposed to the external environment 43, and the second surface 412 has a second breathable area exposed to the cavity 44. The muffler 41 also has multiple breathable channels communicating between the first breathable area and the second breathable area, thereby allowing the gas in the cavity 44 to be discharged from the muffler 41 to the external environment 43.

The low-noise breathing mask 1, which adopts the above-mentioned technical solution, is characterized in that at least one noise reduction component 4 is provided to replace the existing technology of directly opened holes on the mask.

Instead, the noise reduction component 4 is arranged on the wall surface of the mask body 2 that does not directly contact the user's face. One of the key points is that the noise reduction component 4 includes a ventilation opening 42 and a muffler 41. The ventilation opening 42 penetrates the mask body 2 to connect the cavity 44 with the external environment 43. The muffler 41 is connected to the mask body 2 and covers the ventilation opening 42. It can be made of noise reduction materials. Specifically, the muffler 41 has a first surface 411 and a second surface 412. The first surface 411 corresponds to the one facing the outside environment 43, while the second surface 412 corresponds to the one facing the cavity 44 (referred to as the pressurization chamber in this field) and the face. Moreover, the muffler 41 also has multiple breathable channels that communicate with the first and second breathable areas. As shown in FIG. 4, the exhaled gas produced by the user enters the cavity 44 and forms a different exhaust flow path from the pressurized airflow in the cavity 44. The arrowed curve in FIG. 4 indicates the exhaust flow path. The exhaled gas is smoothly guided to the noise reduction component 4 and enters the outside environment 43 through the breathable channels of the muffler 41. That is, the muffler 41 allows the gas in the cavity 44 to be discharged to the external environment 43. Therefore, when wearing the aforementioned low-noise breathing mask 1, gases exhaled by the user, such as carbon dioxide, can continuously be discharged to the external environment 43 through the interior of the aforementioned cavity 44 (referred to as a pressurized chamber in the field) via the noise reduction component 4. The multiple breathable channels in the noise reduction component 41 can disperse the airflow, transforming it from a bundled flow to a less turbulent, smaller stream, significantly reducing the noise generated when the gas in the aforementioned cavity 44 is discharged through the aforementioned noise reduction component 41 to the external environment 43. Additionally, as gases exhaled by the user can continuously flow from the interior of the cavity 44 to the external environment 43, setting the aforementioned noise reduction component 4 can reduce the probability of re-inhaling carbon dioxide exhaled by the user and maintain the treatment pressure inside the cavity 44 during use.

It should be pointed out that there are some flaws in using other forms, such as opening ventilation holes on the frame or elbow joint that comes with the breathing mask as in the prior art. Firstly, such designs could concentrate the airflow and generate noise. Secondly, the noise reduction exhaust device (understood as noise reduction component 4) needs to be kept clean, so the ventilation parts require frequent cleaning or replacement, which would reduce the lifespan of the frame or elbow joint. There is currently a product on the market that places noise reduction materials on the elbow joint, which directly places cotton around the noise reduction exhaust device. Although it achieves noise reduction, the difficulty in cleaning and replacement makes it easy for the cotton to breed bacteria, which reduces the lifespan of the elbow joint. By choosing to directly open a hole on the mask instead of other parts that are not in direct contact with the skin, such as the frame or elbow joint, can reduce unnecessary replacements and prolong the lifespan of other components. At the same time, considering that the mask is the part that is closest to the face and users wear it every day, in order to maintain the sealing effect and cleanliness of the mask, the mask needs to be replaced at short intervals. Therefore, in this application, the noise reduction component 4 (i.e., the noise reduction exhaust device) is set on the mask, which not only reduces user costs but also reduces resource waste. In summary, in this embodiment, the noise reduction component 4 is set on the mask body 2 of the breathing mask, and a muffler 41 is used instead of simply using opening hole(s) directly. This not only disperses the airflow, reduces noise, improves the user's sleep quality and experience, and enhances user friendliness during the treatment process, but also avoids resource waste caused by frequent replacement.

Furthermore, the surface area of the first breathable area is at or between 0.45% to 45% of the outer surface area of the mask body 2, where the outer surface of the mask body 2 is exposed to the external environment 43. This ensures that there is sufficient area in the muffler 41 for gas to be discharged from the cavity 44, allowing gas in the cavity 44 to be smoothly discharged to the external environment 43 without compromising the overall structural strength of the mask.

Figure 6:
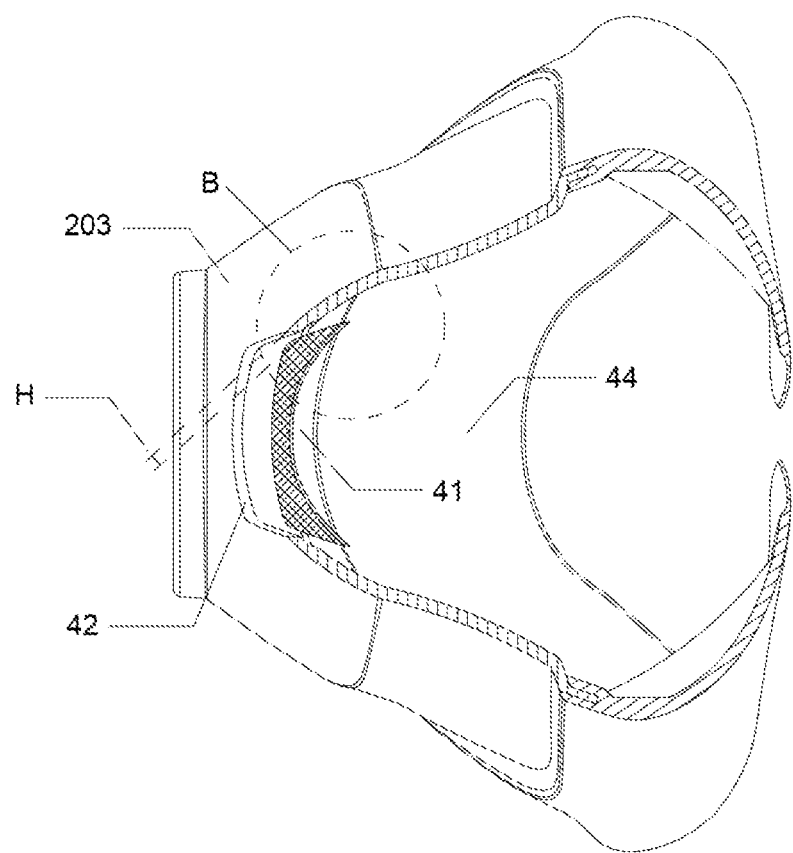
FIG. 6 is a sectional view diagram taken at B-B of FIG. 3.
Figure 7:
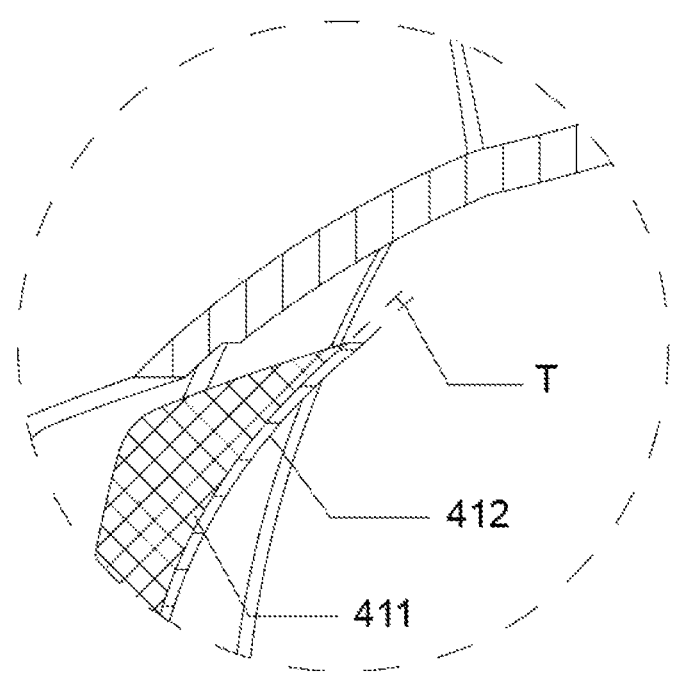
FIG. 7 is an enlarged schematic diagram of location B in FIG. 6.

Further, referring to FIG. 6, which is a sectional view of B-B in FIG. 3, the mask body 2 has a shielding wall 203 with a thickness less than or equal to 5 mm, and the ventilation opening 42 is provided on the shielding wall 203. In other words, the depth H (or thickness) of the ventilation opening 42 is less than or equal to 5 mm. Referring to FIG. 7, which is an enlarged view of A in FIG. 6, the muffler 41 has a thickness T less than or equal to 15 mm. The weight of the muffler 41 is less than or equal to 7 g. The surface area of the first breathable area or the second breathable area is at or between 1-2000 $mm^2$. The muffler 41 is a noise-reducing mesh made of polyvinyl chloride, polypropylene, polytetrafluoroethylene, or nylon. It should be noted that the material, thickness, density, etc. of the muffler 41 determine its noise reduction effect, but the specific choice should be determined based on processing, aesthetics, and actual effects. The material of the muffler 41 should not be too thick. This is because a thick material would reduce gas permeability and compromise the exhaust effect, and also affect the overall appearance and weight of the mask. Therefore, the thickness of the noise reduction material (i.e., the muffler 41) should be no more than 15 mm, and the weight should be no more than 7 g. The surface area of the first breathable area or the second breathable area is at or between 1-2000 $mm^2$. The thickness of the noise reduction material refers to the vertical distance between the first surface 411 and the second surface 412 of the noise reduction material. With this design, the exhaled gas is guided to the noise reduction component 4, and the noise generated when exhaled gas passes through the noise reduction component 4 and enters the external environment 43 does not exceed 30 dB.

In addition, the first surface 411 of the muffler 41 is fixedly connected to the inner surface of the mask body 2, in which the inner surface of the mask body 2 is exposed in the cavity 44. Specifically, the connection between the muffler 41 and the mask body 2 is achieved by an adhesive, snap fastener, buckle, knob, injection molding, ultrasonic welding or heat pressing. This ensures a more stable connection between the muffler 41 and the mask body 2, reducing the likelihood of the muffler falling off.

Figure 5A:
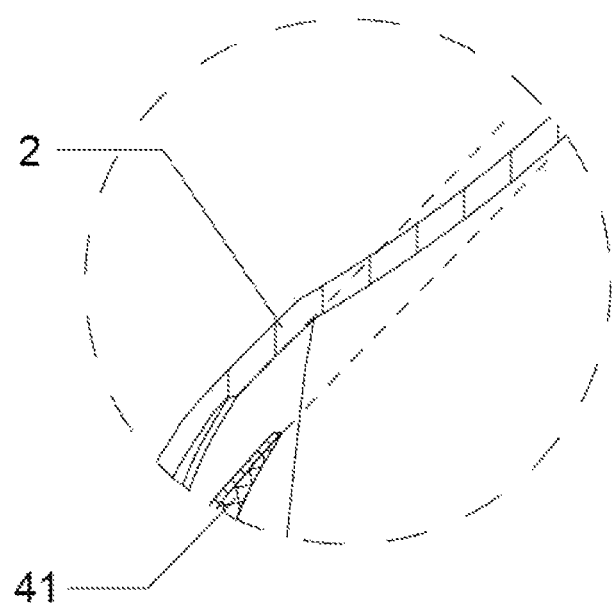
FIG. 5a is an enlarged schematic diagram (1) of location A in FIG. 4.
Figure 5B:
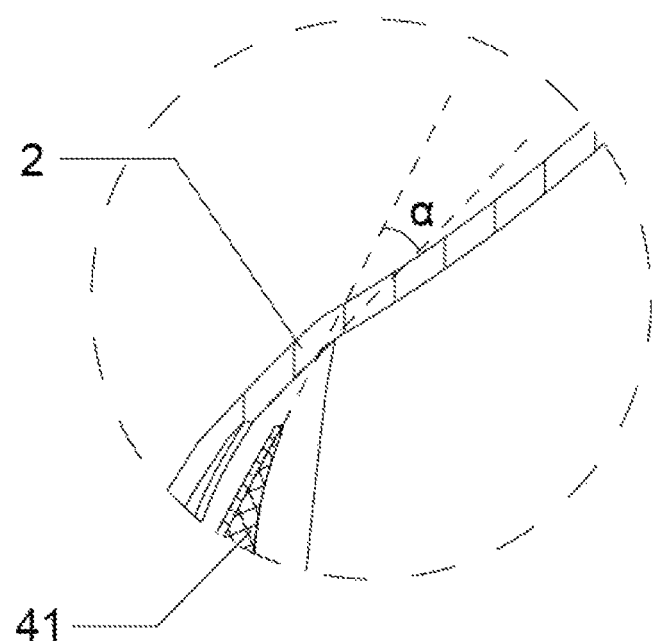
FIG. 5b is an enlarged schematic diagram (2) of location A in FIG. 4.

Furthermore, the angle α between the plane of the first breathable area on the first surface 411 of the muffler 41 and the plane of the portion of the inner surface of the mask body 2 where the muffler 41 is connected is at or between 0-80°. This reduces the possibility of the airflow spraying onto the user's face during exhalation and affecting the user's sleep. Referring to FIG. 5a, which is an enlarged schematic diagram (1) of point A in FIG. 4, the connection between the muffler 41 of the noise reduction component 4 and the mask body 2 is approximately parallel. In FIG. 5a, it can be seen that the plane of the first breathable area on the first surface 411 of the muffler 41 is parallel to the plane of the portion of the inner surface of the mask body 2 connected to the muffler 41. Alternatively, referring to FIG. 5b, which is an enlarged schematic diagram (2) of point A in FIG. 4, the connection between the muffler 41 of the noise reduction component 4 and the mask body 2 is not parallel. In FIG. 5b, it can be seen that the angle α between the plane of the first breathable area on the first surface 411 of the muffler 41 and the plane of the portion of the inner surface of the mask body 2 where the muffler 41 is connected is 30°.

Additionally, the minimum distance between the second surface 412 of the muffler 41 and the plane where the first opening 301 is located is greater than or equal to a preset value, so that when the low-noise breathing mask 1 is worn on the face, the minimum distance between the muffler 41 and the face is greater than or equal to 10 mm. It should be understood that the direction of exhaust should avoid blowing towards the face or other parts that may affect the user's sleep, while also avoiding blockage of the noise reduction component 4 when the wearer is sleeping on their side. Therefore, the position of the noise reduction component 4 should be at a certain distance from the face, with a minimum distance of at least 10 mm in the usage state to avoid discomfort caused by the face pressing against the noise reduction component 4.

It should be noted that in some other embodiments, the noise reduction component 4 can be configured as multiple components, i.e., the low-noise breathing mask 1 includes multiple noise reduction components 4. This can increase the exhaust channels and ensure smooth gas discharge from the cavity 44.

In some other embodiments, the contour of the ventilation opening 42 can be any of circular, elliptical, rectangular, square, or triangular shapes. It should be understood that the ventilation opening 42 can also have other suitable shapes to guide the discharge of gas.

Embodiment 2

Figure 8:
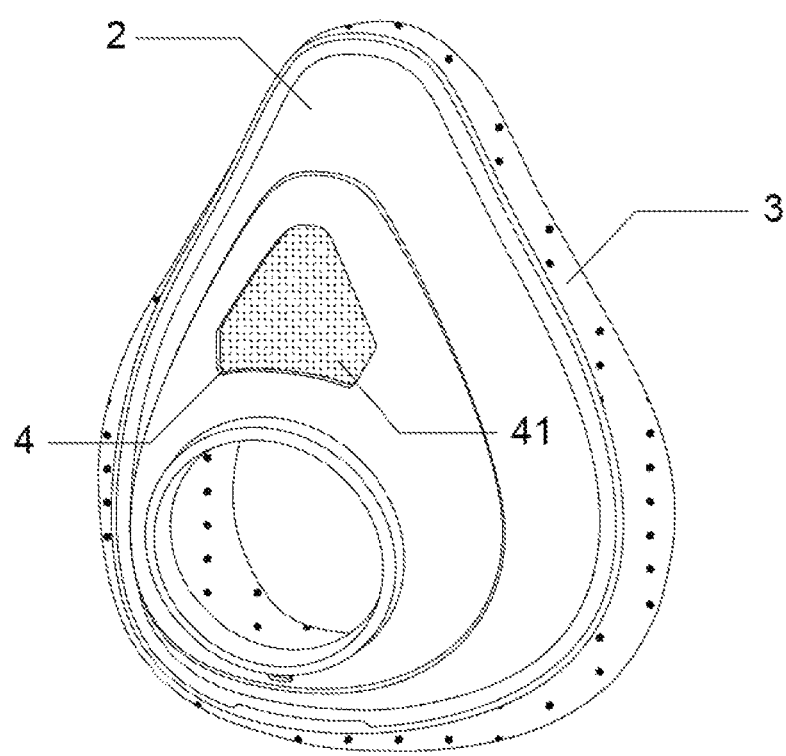
FIG. 8 is a three-dimensional combined schematic diagram of the low-noise breathing mask provided in Embodiment 2.

This embodiment provides a low-noise breathing mask 1, which differs from Embodiment 1, as shown in FIG. 8, which is a three-dimensional combined schematic diagram of the low-noise breathing mask 1 provided in this embodiment. It can be seen in FIG. 8 that the muffler 41 is made of noise reducing cotton. Specifically, the noise reducing cotton is made of one of the materials including polyester, polypropylene, polyethylene, nylon, vinylon, and natural fabrics.

Embodiment 3

Figure 9:
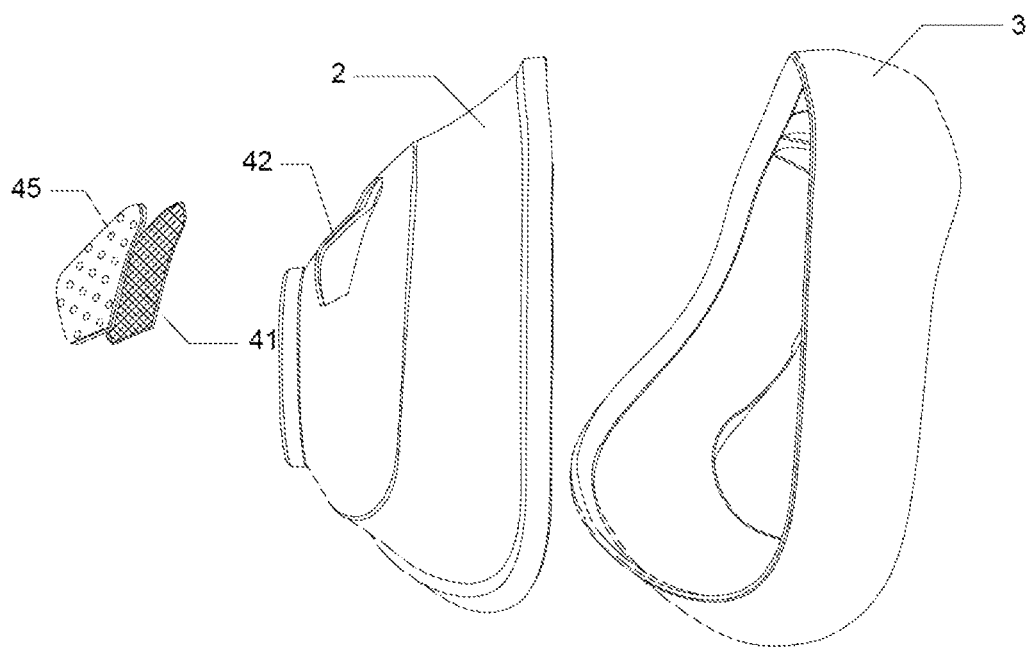
FIG. 9 is a three-dimensional exploded schematic diagram of the low-noise breathing mask provided in Embodiment 3.
Figure 15:
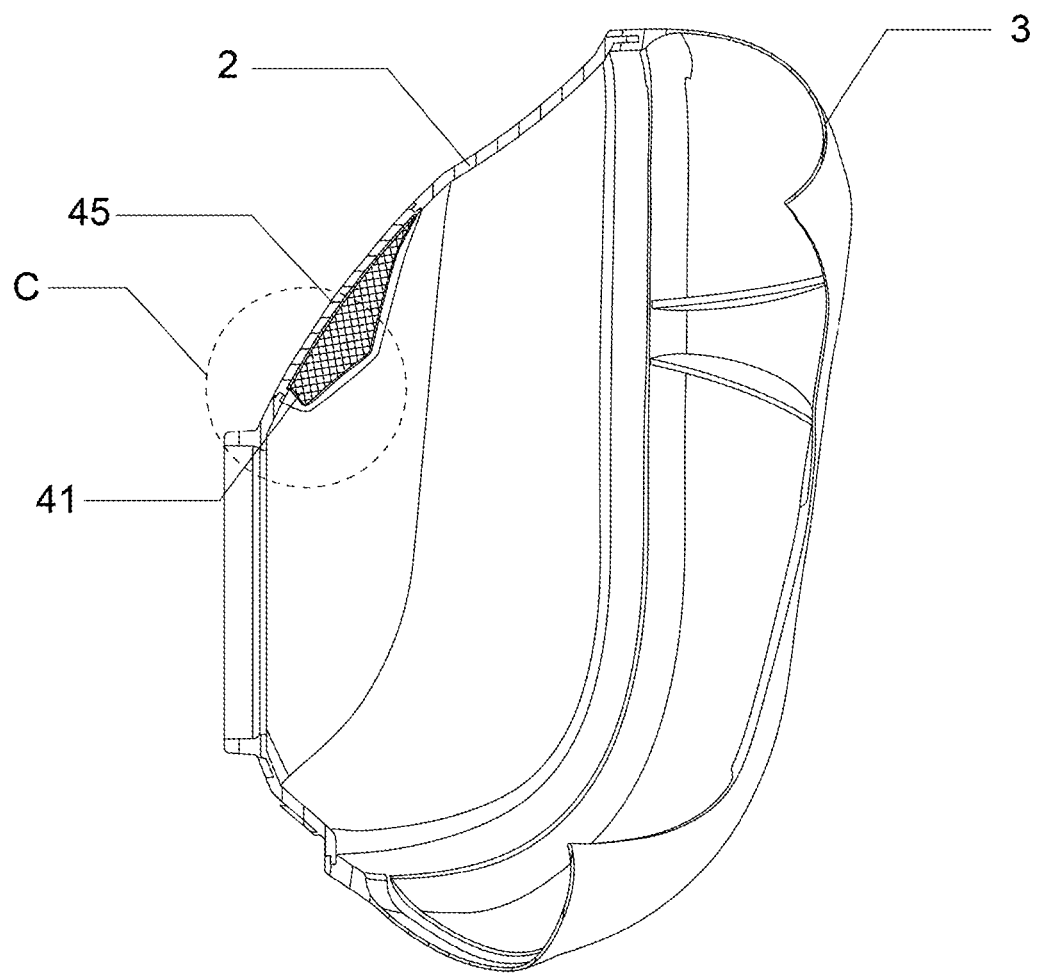
FIG. 15 is a sectional schematic diagram of the low-noise breathing mask provided in Embodiment 3.
Figure 16:
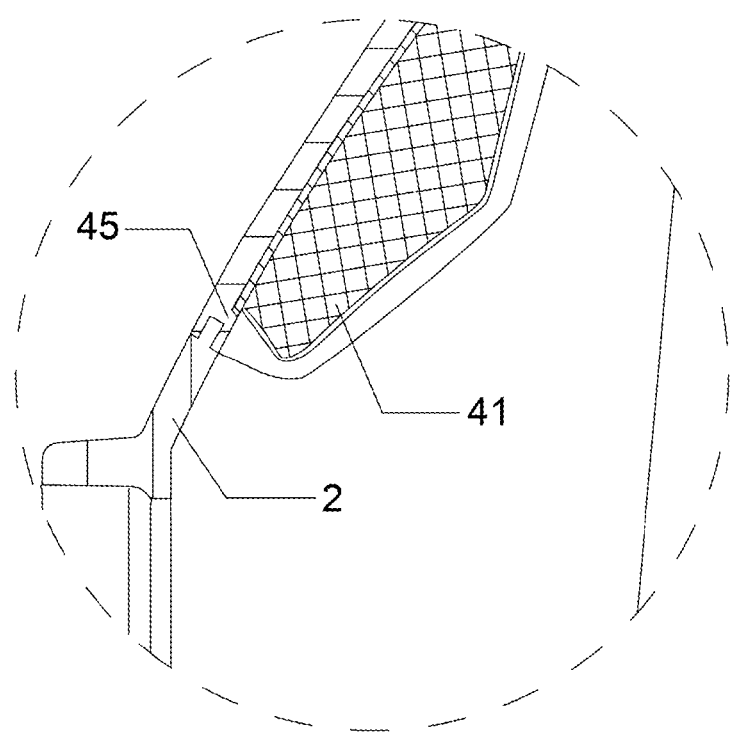
FIG. 16 is an enlarged schematic diagram (1) of point C in FIG. 15.
Figure 17:
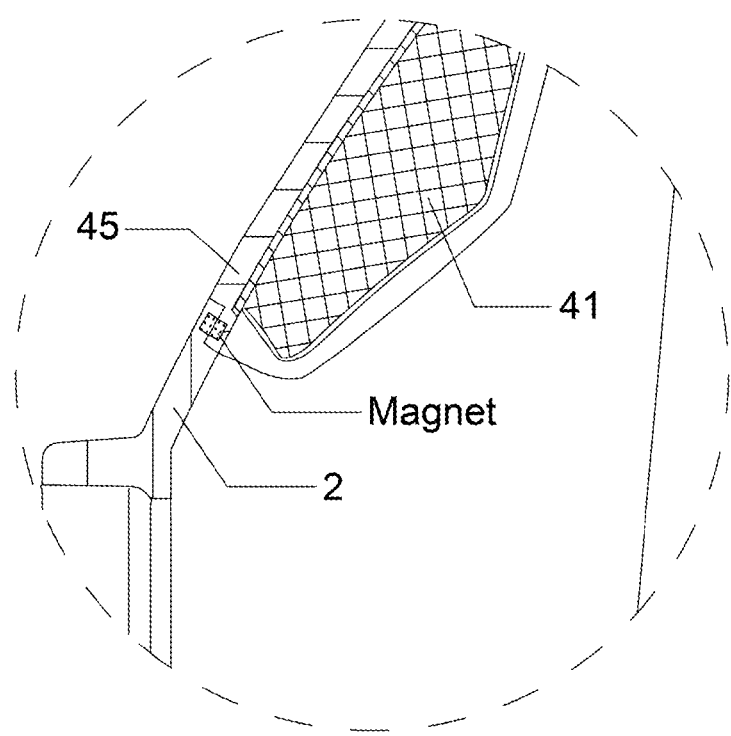
FIG. 17 is an enlarged schematic diagram (2) of point C in FIG. 15.

This embodiment provides a low-noise breathing mask 1, which differs from Embodiment 1 in that the noise reduction component 4 further comprises a casing 45 with multiple through exhaust ports. Specifically, as seen in FIG. 15, a sectional schematic diagram of the low-noise breathing mask and FIG. 9, which is a three-dimensional exploded schematic diagram of the low-noise breathing mask 1 provided in this embodiment, the noise reduction component 41 is attached to one side surface of the casing 45 facing the cavity 44, and the casing 45 has at least one through exhaust port and can be detachably connected to the mask body 2. Specifically, the connection between the casing 45 and the mask body 2 can be achieved through an adhesive, snap fastener (as shown in FIG. 16), buckle, Velcro, knob, magnetic component (as shown in FIG. 17), or clip.

It should be understood that when the air permeability of the noise reduction component 41 is reduced, it can be quickly replaced or washed without the need to deal with the entire low-noise breathing mask 1.

Embodiment 4

Figure 10:
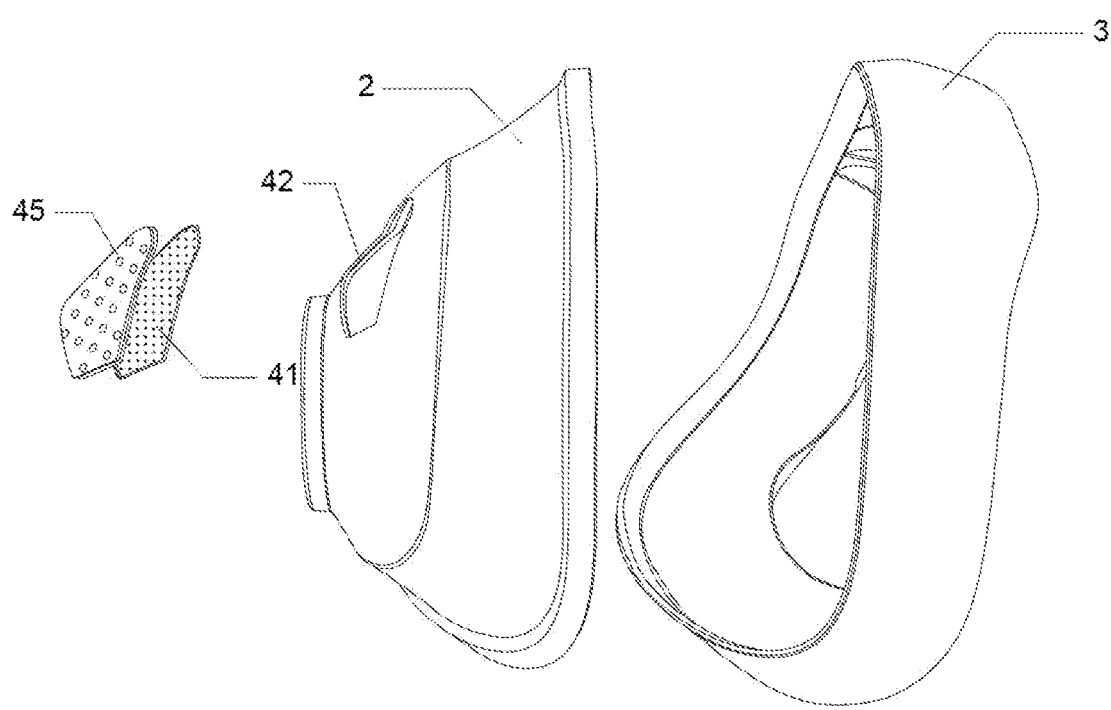
FIG. 10 is a three-dimensional combined schematic diagram of the low-noise breathing mask provided in Embodiment 4.

This embodiment provides a low-noise breathing mask 1, which differs from Embodiment 3 in that, as shown in FIG. 10, which is a three-dimensional combined schematic diagram of the low-noise breathing mask 1 provided in this embodiment, the muffler 41 is made of noise-reducing cotton. Specifically, the noise-reducing cotton is made of a material selected from polyester, polypropylene, polyethylene, nylon, vinylon, and natural fabrics.

Embodiment 5

Figure 11:
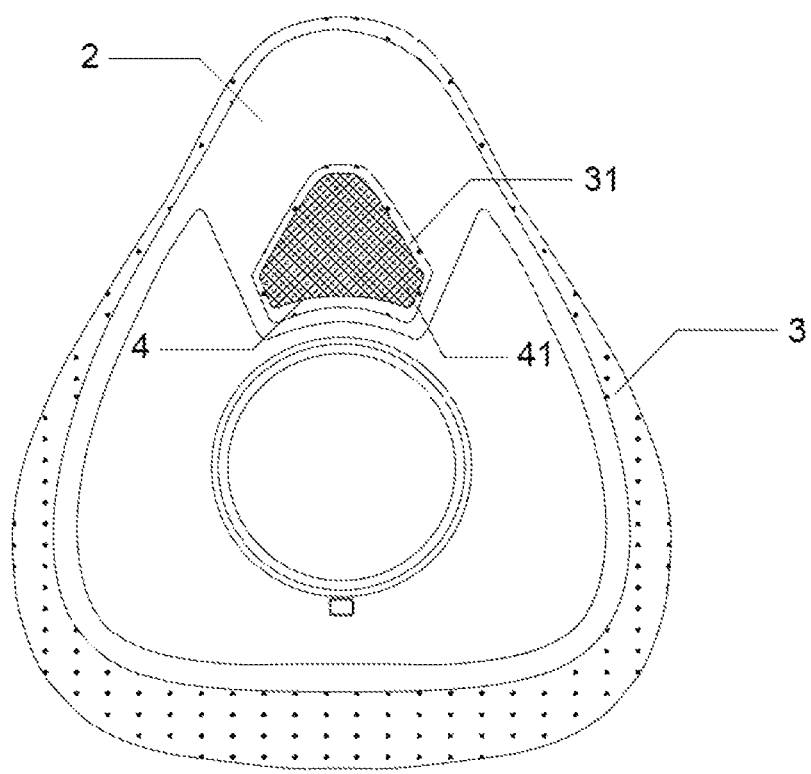
FIG. 11 is a schematic diagram of the front view of the low-noise breathing mask provided in Embodiment 5.

The present embodiment provides a low-noise breathing mask 1, which differs from embodiment 1 in that the design position of the noise reduction component 4 is different. In this embodiment, the noise reduction component 4 is placed on the elastic liner 3. Specifically, as seen in FIG. 11, which is a schematic diagram of the front view of the low-noise breathing mask 1 provided in this embodiment, the low-noise breathing mask 1 also includes an elastic liner 3, a mask body 2, and a noise reduction component 4.

The elastic liner 3 has a fitting side for contacting the user's face and a first connecting side opposite to the fitting side. The fitting side is provided with a first opening 301 through which the user's mouth and nose can pass, and the first connecting side is provided with a second opening 302 that communicates with the first opening 301.

The mask body 2 has a second connecting side and a third connecting side opposite to each other. The second connecting side is provided with a third opening 201 that matches the second opening 302, and the third opening 201 is connected to the second opening 302. The third connecting side is provided with a fourth opening 202 for receiving pressurized gas. The mask body 2 also has a cavity 44 communicating between the third opening 201 and the fourth opening 202.

The noise reduction component 4 includes a ventilation opening 42 and a muffler 41. One of the key points is that the ventilation opening 42 is provided on the elastic liner 3. Specifically, the elastic liner 3 includes a liner extension surface 31 extending toward the fourth opening 202 of the mask body 2 (which can be understood as replacing the shielding wall 203 in embodiment one with the liner extension surface 31 integrated with the elastic liner 3). The ventilation opening 42 is provided on the liner extension surface 31. The muffler 41 has a first surface 411 facing the external environment 43 and a second surface 412 opposite to the first surface 411. The first surface 411 has a first breathable area exposed to the external environment 43, and the second surface 412 has a second breathable area exposed to the cavity 44. The muffler 41 also has multiple breathable channels that communicate the first breathable area and the second breathable area, allowing the gas inside the cavity 44 to discharge to the external environment 43 through the muffler 41.

When wearing the low-noise breathing mask 1, the gas exhaled by the user, such as carbon dioxide, can continuously be discharged from the inside of the cavity 44 (also referred to as a pressurization chamber in this field) through the noise reduction component 4 to the external environment 43. The multiple breathable channels contained in the muffler 41 can disperse the gas flow and make the mass of gas flow into smaller and less turbulent gas flows, thereby significantly reducing the noise when the gas inside the cavity 44 is discharged to the external environment 43 through the muffler 41. The noise reduction effect is surprisingly greater.

Embodiment 6

Figure 12:
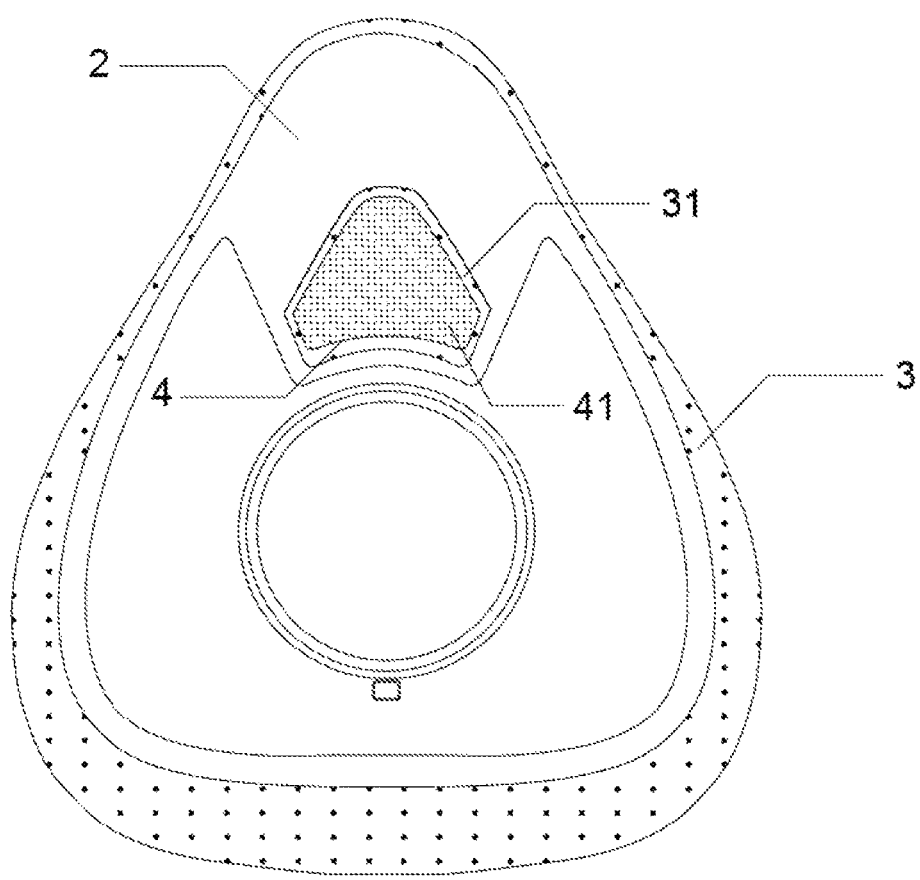
FIG. 12 is a three-dimensional combined schematic diagram of the low-noise breathing mask provided in Embodiment 6.

This embodiment provides a low-noise breathing mask 1, which differs from Embodiment 5 as shown in FIG. 12. FIG. 12 is a three-dimensional combined schematic diagram of the low-noise breathing mask 1 provided, in which the muffler 41 is made of noise reducing cotton. Specifically, the noise reducing cotton is made of a material selected from polyester, polypropylene, polyethylene, nylon, vinyl, and natural fabrics.

Embodiment 7

Figure 13:
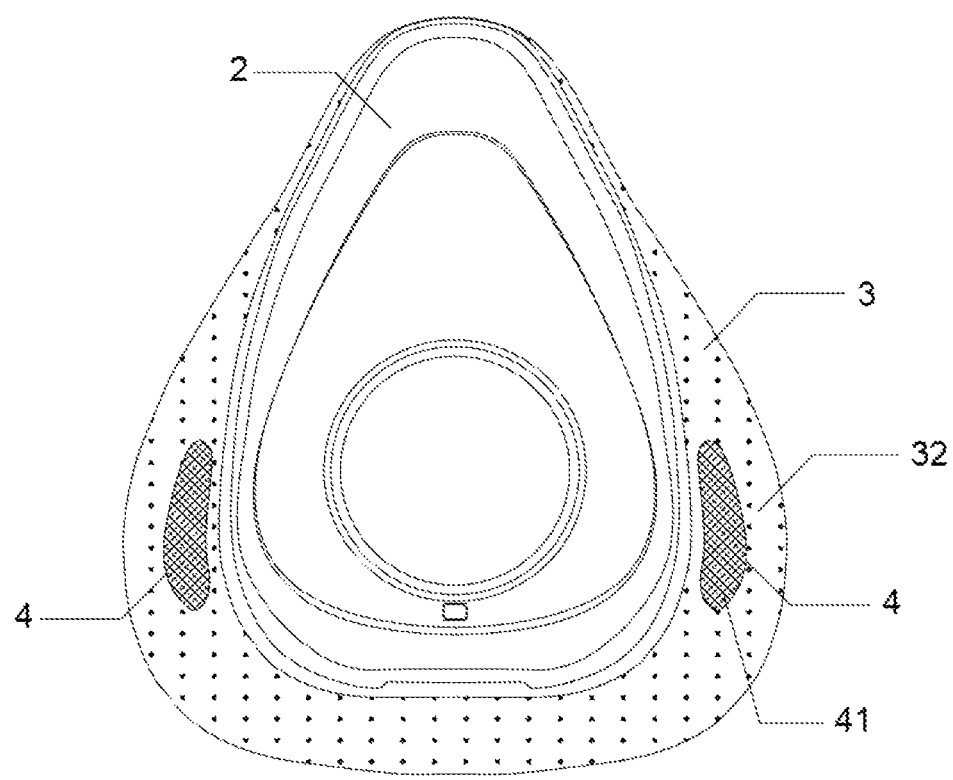
FIG. 13 is a schematic diagram of the front view of the low-noise breathing mask provided in Embodiment 7.

This embodiment provides a low-noise breathing mask 1, which differs from embodiment 1 in the design position of the noise reduction component 4. In this embodiment, the noise reduction component 4 is set on the elastic liner 3. As seen in FIG. 13, which is a schematic diagram of the front view of the low-noise breathing mask 1, the low-noise breathing mask 1 also includes an elastic liner 3, a mask body 2, and a noise reduction component 4.

The elastic liner 3 has a fitting side for contacting the user's face and a first connecting side opposite to the fitting side. The fitting side is provided with a first opening 301 that can be passed through by the user's mouth and nose, and the first connecting side is provided with a second opening 302 that communicates with the first opening 301.

The mask body 2 has a second connecting side and a third connecting side opposite to each other. The second connecting side is provided with a third opening 201 that matches the second opening 302, and the third opening 201 is connected to the second opening 302. The third connecting side is provided with a fourth opening 202 for receiving pressurized gas. The mask body 2 also has a cavity 44 communicating between the third opening 201 and the fourth opening 202.

The noise reduction component 4 includes a ventilation opening 42 and a muffler 41. The key is that the ventilation opening 42 is opened on the elastic liner 3. Specifically, the elastic liner 3 includes a liner bottom surface for abutting the user's face and a liner side surface 32 surrounding the liner bottom surface, and the ventilation opening 42 is opened on the liner side surface 32. The muffler 41 has a first surface 411 facing the external environment 43 and a second surface 412 opposite to the first surface 411. The first surface 411 has a first breathable area exposed to the external environment 43, and the second surface 412 has a second breathable area exposed to the cavity 44. The muffler 41 also has multiple breathable channels that communicate the first breathable area and the second breathable area, thereby allowing the gas inside the cavity 44 to continuously discharge to the external environment 43 through the muffler 41.

Obviously, when wearing the low-noise breathing mask 1, the gas exhaled by the user, such as carbon dioxide, can be continuously discharged from the inside of the cavity 44 (referred to as the pressurization chamber in this field) through the noise reduction component 4 to the external environment 43. The multiple breathable channels contained in the muffler 41 can disperse the airflow, making the bundled airflow into more smaller airflows, thereby significantly reducing the noise when the gas inside the cavity 44 is discharged to the external environment 43 through the muffler 41, and the noise reduction effect is remarkably improved.

Furthermore, multiple noise reduction components 4 are symmetrically or asymmetrically arranged on the elastic liner 3. In this way, the exhaust channels can be increased to ensure that the gas inside the cavity 44 is smoothly discharged.

Embodiment 8

Figure 14:
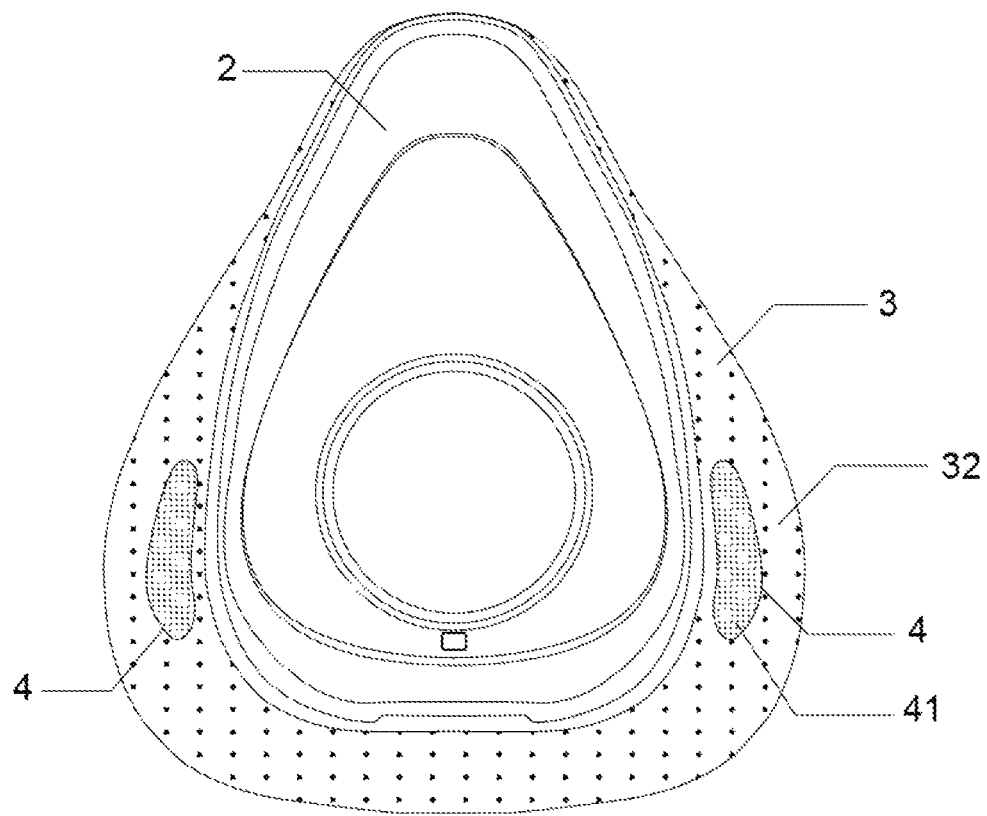
FIG. 14 is a three-dimensional combined schematic diagram of the low-noise breathing mask provided in Embodiment 8.

This embodiment provides a low-noise breathing mask 1, which differs from Embodiment 7 as shown in FIG. 14. FIG. 14 is a three-dimensional combined schematic diagram of the low-noise breathing mask 1 in which the muffler 41 is made of noise-reducing cotton. Specifically, the noise-reducing cotton is made of a material selected from polyester, polypropylene, polyethylene, nylon, vinyl, and natural fabrics.

Aspects:

Aspects 1-16 can be combinable with any of Aspects 17-20, any of Aspects 17-18 can be combinable with any of Aspects 1-16 and 19-20, Aspect 19 can be combinable with any of Aspects 1-18 and 20, and Aspect 20 can be combinable with any of Aspects 1-19.

Aspect 1: A low-noise breathing mask comprising: an elastic liner having a fitting side configured to contact a face of a user and a first connecting side opposite to the fitting side, the fitting side having a first opening through which a mouth and nose of the user can pass, and the first connecting side having a second opening that communicates with the first opening; a mask body having a second connecting side and a third connecting side opposite to each other, the second connecting side having a third opening that matches the second opening, and the third opening being connected to the second opening, the third connecting side having a fourth opening for receiving pressurized gas, the mask body also having a cavity communicating between the third opening and the fourth opening; and a noise reduction component comprising a ventilation opening and a muffler, the ventilation opening being provided in the mask body and communicating with the third opening, the muffler being connected to the mask body and covering the ventilation opening, the muffler having a first surface facing an external environment and a second surface opposite to the first surface, the first surface having a first breathable area exposed to the external environment, and the second surface having a second breathable area exposed to the cavity, wherein the muffler further comprises multiple breathable channels that communicate with the first breathable area and the second breathable area, and configured to allow gas in the cavity to be discharged to the external environment through the muffler.

Aspect 2. The low-noise breathing mask according to Aspect 1, wherein a surface area of the first breathable area is at or between 0.45% to 45% of an outer surface area of the mask body, and the outer surface area of the mask body is exposed to the external environment.

Aspect 3. The low-noise breathing mask according to any of Aspects 1-2, wherein the mask body has a shielding wall with a thickness of less than or equal to 5 mm, and the ventilation opening is provided in the shielding wall.

Aspect 4. The low-noise breathing mask according to any of Aspects 1-3, wherein the muffler has a thickness of less than or equal to 15 mm.

Aspect 5. The low-noise breathing mask according to any of Aspects 1-4, wherein an area of the first breathable area or an area of the second breathable area is between 1-2000 mm$^2$.

Aspect 6. The low-noise breathing mask according to any of Aspects 1-5, wherein a weight of the muffler is of less than or equal to 7 g.

Aspect 7. The low-noise breathing mask according to any of Aspects 1-6, comprising multiple noise reduction components.

Aspect 8. The low-noise breathing mask according to any of Aspects 1-7, wherein a contour of the ventilation opening is circular, elliptical, rectangular, square, or triangular.

Aspect 9. The low-noise breathing mask according to any of Aspects 1-8, wherein the noise reduction component further comprises a casing, and the muffler is attached to one side surface of the casing facing the cavity, the casing having at least one through exhaust port, and the casing being detachably connectable to the mask body.

Aspect 10. The low-noise breathing mask according to Aspect 9, wherein the casing is connected to the mask body by an adhesive, snap fastener, buckle, Velcro, knob, magnetic component, or clip.

Aspect 11. The low-noise breathing mask according to any of Aspects 1-10, wherein the muffler is fixedly connected to the mask body.

Aspect 12. The low-noise breathing mask according to Aspect 11, wherein the muffler is connected to the mask body by an adhesive, buckle, knob, clip, ultrasonic welding, or heat pressing.

Aspect 13. The low-noise breathing mask according to any of Aspects 1-12, wherein the muffler is made of noise reducing cotton or noise reducing mesh.

Aspect 14. The low-noise breathing mask according to Aspect 13, wherein the noise reducing cotton is made of a material selected from polyester, polypropylene, polyethylene, nylon, vinylon, and natural fabric; the noise reducing mesh is made of a material selected from polyvinyl chloride, polypropylene, polytetrafluoroethylene, or nylon.

Aspect 15. The low-noise breathing mask according to any of Aspects 1-14, wherein an angle between a plane in which the first breathable area of the first surface of the muffler is located and a plane in which an inner surface of the mask body is connected to the muffler is at or between 0-80°.

Aspect 16. The low-noise breathing mask according to any of Aspects 1-15, wherein a minimum distance between the second surface of the muffler and a plane in which the first opening is located is greater than or equal to a preset value so that when the low-noise breathing mask is worn on the face of the user, the minimum distance between the muffler and the face of the user is greater than or equal to 10 mm.

Aspect 17. A low-noise breathing mask comprising: an elastic liner with a fitting side for contacting a face of a user and a first connecting side opposite to the fitting side, the fitting side having a first opening for a mouth and nose for the user to pass through, and the first connecting side having a second opening connected to the first opening; a mask body with a second connecting side and a third connecting side opposite to each other, the second connecting side having a third opening matching the second opening, the third opening connected to the second opening, and the third connecting side having a fourth opening for receiving pressurized gas, the mask body also having a cavity connecting the third opening and the fourth opening; and a noise reduction component including a ventilation opening and a muffler, the ventilation opening being provided in the elastic liner, the muffler having a first surface facing an external environment and a second surface opposite the first surface, the first surface having a first breathable area exposed to the external environment, and the second surface having a second breathable area exposed to the cavity, wherein the muffler further comprises multiple breathable channels connecting the first breathable area and the second breathable area, allowing the gas in the cavity to be discharged from the muffler to the external environment.

Aspect 18. The low-noise breathing mask according to Aspect 17, further comprising a plurality of noise reduction components, the plurality of noise reduction components being arranged symmetrically or asymmetrically on said elastic liner.

Aspect 19. A low-noise breathing mask comprising: an elastic liner having a fitting side for contacting a user's face and a first connecting side opposite to the fitting side, the fitting side being provided with a first opening through which a user's mouth and nose is configured to pass, and the first connecting side being provided with a second opening communicating with the first opening; a mask body having a second connecting side and a third connecting side opposite to each other, the second connecting side being provided with a third opening matching the second opening, the third opening being connected to the second opening, and the third connecting side being provided with a fourth opening for receiving pressurized gas, the mask body also having a cavity communicating between the third opening and the fourth opening; and a noise reduction component comprising a ventilation opening and a muffler, the ventilation opening being provided in the mask body and communicating with the third opening, the muffler being connected to the mask body and covering the ventilation opening, the muffler having a first surface facing an external environment and a second surface opposite to the first surface, the first surface having a first breathable area exposed to the external environment, and the second surface having a second breathable area exposed to the cavity; the muffler also having multiple breathable channels connecting the first breathable area and the second breathable area, allowing gas in the cavity to be discharged from the muffler to the external environment, wherein a surface area of the first breathable area is at or between 0.45% to 45% of a surface area of an outer surface of the mask body, which communicates with the external environment, and wherein the mask body has a shielding wall with a thickness of less than or equal to 5 mm, and the ventilation opening is provided in the shielding wall.

Aspect 20. A low-noise breathing mask, comprising: an elastic liner with a fitting side for contacting a user's face and a first connecting side opposite to the fitting side, the fitting side having a first opening for a user's mouth and nose to pass through, and the first connecting side having a second opening communicating with the first opening; a mask body with a second connecting side and a third connecting side opposite to each other, the second connecting side having a third opening matching the second opening and connected to it, and the third connecting side having a fourth opening for receiving pressurized gas, the mask body also having a cavity communicating between the third opening and the fourth opening; and a noise reduction component comprising a ventilation opening and a muffler, the ventilation opening being provided in the mask body and communicating with the third opening, the muffler being connected to the mask body and covering the ventilation opening, the muffler having a first surface facing an external environment and a second surface opposite to the first surface, the first surface having a first breathable area exposed to the external environment, and the second surface having a second breathable area exposed to the cavity; the muffler also has multiple breathable channels communicating the first breathable area and the second breathable area, allowing the gas in the cavity to be discharged from the muffler to the external environment, wherein the muffler has a thickness that is less than or equal to 15 mm, an area of the first breathable area or the second breathable area is at or between 1-2000 mm$^2$; and a weight of the muffler is of less than or equal to 7 g.

The above description of the embodiments of the disclosure has been made in conjunction with the accompanying drawings. However, the disclosure is not limited to the specific embodiments described above, which are only illustrative rather than restrictive. Ordinary skilled persons in the art may make many other forms of embodiments based on the inspiration of the disclosure, within the scope of the purpose and the protection scope of the claims of the disclosure.

The invention claimed is:

1. A low-noise breathing mask comprising:
   an elastic liner having a fitting side configured to contact a face of a user and a first connecting side opposite to the fitting side, the fitting side having a first opening through which a mouth and nose of the user can pass, and the first connecting side having a second opening that communicates with the first opening;
   a mask body having a second connecting side and a third connecting side opposite to each other, the second connecting side having a third opening that matches the second opening, and the third opening being connected to the second opening, the third connecting side having a fourth opening for receiving pressurized gas, the mask body also having a cavity communicating between the third opening and the fourth opening; and
   a noise reduction component comprising a ventilation opening and a muffler, the ventilation opening being provided in the mask body and communicating with the third opening, the muffler being connectable to the mask body and covering the ventilation opening, the muffler having a first surface facing an external environment and a second surface opposite to the first surface, the first surface having a first breathable area exposed to the external environment, and the second surface having a second breathable area exposed to the cavity,
   wherein the muffler further comprises multiple breathable channels that connect the first breathable area and the second breathable area to allow gas in the cavity to be discharged and dispersed into smaller streams to the external environment through the muffler,
   wherein the muffler is made of noise reducing cotton or noise reducing mesh,
   wherein a portion of the first surface of the muffler is connectable to an inner surface of the mask body, and
   wherein the muffler has a thickness of less than or equal to 15 mm.

2. The low-noise breathing mask according to claim 1, wherein a surface area of the first breathable area is at or between 0.45% to 45% of an outer surface area of the mask body, and the outer surface area of the mask body is exposed to the external environment.

3. The low-noise breathing mask according to claim 1, wherein the mask body has a shielding wall with a thickness of less than or equal to 5 mm, and the ventilation opening is provided in the shielding wall.

4. The low-noise breathing mask according to claim 1, wherein an area of the first breathable area or an area of the second breathable area is between 1-2000 mm$^2$.

5. The low-noise breathing mask according to claim 1, wherein a weight of the muffler is of less than or equal to 7 g.

6. The low-noise breathing mask according to claim 1, comprising multiple noise reduction components.

7. The low-noise breathing mask according to claim 1, wherein a contour of the ventilation opening is circular, elliptical, rectangular, square, or triangular.

8. The low-noise breathing mask according to claim 1, wherein the noise reduction component further comprises a casing, and the muffler is attached to one side surface of the casing facing the cavity, the casing having at least one through exhaust port, and the casing being detachably connectable to the mask body.

9. The low-noise breathing mask according to claim 8, wherein the casing is connected to the mask body by an adhesive, snap fastener, buckle, hook and loop fasteners, knob, magnetic component, or clip.

10. The low-noise breathing mask according to claim 1, wherein the muffler is fixedly connected to the mask body.

11. The low-noise breathing mask according to claim 1, wherein the noise reducing cotton is made of a material selected from polyester, polypropylene, polyethylene, nylon, vinylon, and natural fabric; the noise reducing mesh is made of a material selected from polyvinyl chloride, polypropylene, polytetrafluoroethylene, or nylon.

12. The low-noise breathing mask according to claim 1, wherein an angle between a plane in which the first breathable area of the first surface of the muffler is located and a plane in which an inner surface of the mask body is connected to the muffler is at or between 0-80°.

13. The low-noise breathing mask according to claim 1, wherein a minimum distance between the second surface of the muffler and a plane in which the first opening is located is greater than or equal to a preset value so that when the low-noise breathing mask is worn on the face of the user, the minimum distance between the muffler and the face of the user is greater than or equal to 10 mm.

14. The low-noise breathing mask according to claim 1, wherein a connection between the first surface of the muffler and the inner surface of the mark body is either parallel or at an angle α between a plane of the first breathable area on the first surface and a plane of a portion of the inner surface of the mask body.

15. A low-noise breathing mask comprising:
   an elastic liner with a fitting side for contacting a face of a user and a first connecting side opposite to the fitting side, the fitting side having a first opening for a mouth and nose for the user to pass through, and the first connecting side having a second opening connected to the first opening;
   a mask body with a second connecting side and a third connecting side opposite to each other, the second connecting side having a third opening matching the second opening, the third opening connected to the second opening, and the third connecting side having a fourth opening for receiving pressurized gas, the mask body also having a cavity connecting the third opening and the fourth opening; and
   a noise reduction component including a ventilation opening and a muffler, the ventilation opening being provided in the elastic liner, the muffler having a first surface facing an external environment and a second surface opposite the first surface, the first surface having a first breathable area exposed to the external environment, and the second surface having a second breathable area exposed to the cavity, wherein the muffler further comprises multiple breathable channels that connect the first breathable area and the second breathable area to allow gas in the cavity to be discharged and dispersed into smaller streams from the muffler to the external environment, wherein a portion of the first surface of the muffler is connectable to an inner surface of the elastic liner, wherein the muffler is made of noise reducing cotton or noise reducing mesh, and wherein the muffler has a thickness of less than or equal to 15 mm.

16. The low-noise breathing mask according to claim 15, further comprising a plurality of noise reduction components, the plurality of noise reduction components being arranged symmetrically or asymmetrically on said elastic liner.

17. A low-noise breathing mask comprising:

an elastic liner having a fitting side for contacting a user's face and a first connecting side opposite to the fitting side, the fitting side being provided with a first opening through which a user's mouth and nose is configured to pass, and the first connecting side being provided with a second opening communicating with the first opening;

a mask body having a second connecting side and a third connecting side opposite to each other, the second connecting side being provided with a third opening matching the second opening, the third opening being connected to the second opening, and the third connecting side being provided with a fourth opening for receiving pressurized gas, the mask body also having a cavity communicating between the third opening and the fourth opening; and a noise reduction component comprising a ventilation opening and a muffler, the ventilation opening being provided in the mask body and communicating with the third opening, the muffler being connectable to the mask body and covering the ventilation opening, the muffler having a first surface facing an external environment and a second surface opposite to the first surface, the first surface having a first breathable area exposed to the external environment, and the second surface having a second breathable area exposed to the cavity; the muffler also having multiple breathable channels that connect the first breathable area and the second breathable area-to allow gas in the cavity to be discharged and dispersed into smaller streams from the muffler to the external environment, wherein the muffler is made of noise reducing cotton or noise reducing mesh, wherein the muffler has a thickness of less than or equal to 15 mm, wherein a portion of the first surface of the muffler is connectable to an inner surface of the mask body, and wherein a surface area of the first breathable area is at or between 0.45% to 45% of a surface area of an outer surface of the mask body, which communicates with the external environment, and wherein the mask body has a shielding wall with a thickness of less than or equal to 5 mm, and the ventilation opening is provided in the shielding wall.

18. A low-noise breathing mask, comprising:

an elastic liner with a fitting side for contacting a user's face and a first connecting side opposite to the fitting side, the fitting side having a first opening for a user's mouth and nose to pass through, and the first connecting side having a second opening communicating with the first opening;

a mask body with a second connecting side and a third connecting side opposite to each other, the second connecting side having a third opening matching the second opening and connected to it, and the third connecting side having a fourth opening for receiving pressurized gas, the mask body also having a cavity communicating between the third opening and the fourth opening; and a noise reduction component comprising a ventilation opening and a muffler, the ventilation opening being provided in the mask body and communicating with the third opening, the muffler being connectable to the mask body and covering the ventilation opening, the muffler having a first surface facing an external environment and a second surface opposite to the first surface, the first surface having a first breathable area exposed to the external environment, and the second surface having a second breathable area exposed to the cavity; the muffler also having multiple breathable channels that connect the first breathable area and the second breathable area to allow gas in the cavity to be discharged and dispersed into smaller streams from the muffler to the external environment, wherein the muffler is made of noise reducing cotton or noise reducing mesh, wherein a portion of the first surface of the muffler is connectable to an inner surface of the mask body, and wherein the muffler has a thickness that is less than or equal to 15 mm, an area of the first breathable area or the second breathable area is at or between 1-2000 $mm^2$; and a weight of the muffler is of less than or equal to 7 g.

* * * * *